United States Patent [19]

Polaschegg

[11] Patent Number: 4,634,430
[45] Date of Patent: Jan. 6, 1987

[54] PUMP ARRANGEMENT FOR MEDICAL PURPOSES

[75] Inventor: Hans-Dietrich Polaschegg, Oberursel, Fed. Rep. of Germany

[73] Assignee: Fresenius Ag, Bad Homburg, Fed. Rep. of Germany

[21] Appl. No.: 709,167

[22] Filed: Mar. 7, 1985

[30] Foreign Application Priority Data

Apr. 15, 1985 [DE] Fed. Rep. of Germany ....... 3408331

[51] Int. Cl.⁴ ............................................. A61M 37/00
[52] U.S. Cl. .................................. 604/141; 604/153; 604/4; 128/DIG. 12; 417/395
[58] Field of Search ............... 604/153, 129, 123, 126, 604/4, 9, 10, 151, 152, 118, 121, 141, 147, 120; 128/202.12, 202.21, 204.18, 1 D; 417/395, 411, 384, 386, 387, 389

[56] References Cited

U.S. PATENT DOCUMENTS

| 2,311,229 | 4/1941 | Herbert | 417/395 |
| 2,855,144 | 10/1958 | Andreasen | 417/389 |
| 3,213,804 | 12/1961 | Sobey | 417/395 |
| 4,265,600 | 5/1981 | Mandroian | 417/395 |
| 4,303,376 | 12/1981 | Siekmann | 417/395 |
| 4,552,552 | 11/1985 | Polaschegg et al. | 128/1 D |

FOREIGN PATENT DOCUMENTS 716399 10/1954 United Kingdom ................ 417/386

Primary Examiner—Stephen C. Pellegrino
Assistant Examiner—John D. Ferros
Attorney, Agent, or Firm—Townsend & Townsend

[57] ABSTRACT

Pump arrangement (10) for medical purposes, in particular blood or infusion pump, comprising a pump housing (12) having two pump chambers (16, 18), of which the work chamber (16) is subjected to the liquid to be pumped while the drive chamber (18) is connected via a connecting conduit to a pneumatic pump (14) of restricted pumping volume.

This connecting conduit (50) comprises a valve (56) which is opened at the respective changeover point (top and bottom dead-center) of the pump (14) to set the entire pump arrangement (16) to atmospheric pressure.

19 Claims, 4 Drawing Figures

PUMP ARRANGEMENT FOR MEDICAL PURPOSES

BACKGROUND OF THE INVENTION

The invention relates to a pump arrangement for medical purposes, in particular a blood or infusion pump, comprising at least one pump housing having a chamber which is divided by an impermeable diaphragm into a working chamber and a drive chamber, the working chamber being provided with at least one opening for the supply and discharge of the fluid to be conveyed and the drive chamber being adapted to be subjected to air as pumping fluid and connected to a pump having a limited pumping volume, and a valve connected to the drive chamber for pressure compensation on stroke change of the pump.

A pump arrangement of the type mentioned at the beginning is known from DE-OS No. 3,205,449 (corresponding to U.S. patent application Ser. No. 466,645 filed Feb. 15, 1983). It consists substantially of a reservoir vessel which is divided into two chambers. The one chamber can be filled and emptied with the fluid to be pumped, in particular blood, whilst the other chamber alternately thereto is subjected to air as pumping fluid. Between these two chambers a resiliently extensible impermeable diaphragm is provided which according to this German specification as laid open to inspection is in the form of a resilient flexible tube. The two chambers are surrounded by a rigid air-impermeable pump housing which for the chamber containing the pumping fluid has an opening which is connected via a conduit to the pump having a limited pumping volume. This pump is constructed as bellows pump which in pumping operation oscillates between the upper and lower dead-centre.

The chamber adapted to be subjected to the pumping fluid or the space containing the pumping fluid is connected via vacuum and pressure control valves to the surroundings. The purpose of these valves is to maintain a certain pressure value, that is a certain excess pressure and reduce pressure in the operation of the pump. If for example the pump is blocked or the usual starting difficulties occur only a supplying or discharge of the pumping fluid takes place until the pressure value controlled by the valves is achieved, which usually operate automatically.

However, usually pumping operation takes place in such a manner that the excess pressure and reduced pressure control valves are not actuated. In such a mode of operation the pumping fluid is thus compressed on discharge of the pumping chamber (excess pressure) and expanded (reduced pressure) on filling of the pumping chamber. However, when operating the pump arrangement problems are encountered which in particular affect the pumping capacity of this arrangement.

Below, the mode of operation of the known pumps and the problems involved will be explained.

As already mentioned the pressure in the pump fluctuates between a lower pressure value $p_{min}$ and an upper pressure value $p_{max}$ at which the valves are just on the point of opening.

Now, depending on the use of the pump a predetermined suction pressure $p_E$ and delivery pressure $p_K$ is required which are to be applied to the pump arrangement.

Assuming that for the diaphragm no force is required for the expansion then in the limit case $p_E = p_{min}$ or $p_K = p_{max}$.

The pumping behavior of the known pump will now be explained with reference to the following example:

$p_E = -400$ mbar and $p_K = +600$ mbar whilst the internal volume of the pumping chamber $V_1 = 50$ cm$^3$ and the bellows volume of the bellows pump $V_2 = 30$ cm$^3$.

In the initial state $V_1$ (compressed) $= 0$ cm$^3$ and $V_2 = 30$ cm$^3$ whilst $p = p_{max} = +600$ mbar absolute $= 1600$ mbar.

Subsequently, suction takes place and $V_1$ approaches 50 cm$^3$ and $V_2$ approaches 0 cm$^3$. The volume is thus expanded from 30 to 50 cm$^3$.

From the relationship $p \times V = a$ constant there follows:

$1600 \times 30 = p_E \times 50$ $p_E = 960$ mbar.

As a result the expansion reduced pressure $p_E$ is only $-40$ mbar abs., and this is not adequate for operating the pump.

If now on expansion of the bellows pump $-400$ mbar is to be attained as explained below a lower pumping volume is merely obtained. For it follows from the above relationship that:

$1600 \times 30 = 600 \times V_T$    ($V_T =$ necessary bellows volume)

$V_T = 80$ cm$^3$ i.e. in the limit case although the suction reduced pressure or vacuum can be reached the bellows volume of 50 cm$^3$ is not adequate for a complete discharge. For this purpose 80 cm$^3$ is required.

A further pump arrangement is known from U.S. Pat. No. 3,568,214 in which two pumping chambers are alternately subjected to pumping fluid from a pump, isotomic saline solution or mercury being used as pumping fluid. The displacement of the phase position on stroke change of the pump occurring in such systems considerably affects the action of the pump and usually cannot be controlled so that this pump has proved impracticable.

The invention is therefore based on the problem of providing a pump arrangement of the type mentioned at the beginning which within the set pressure limits in operation completely fills and empties the pumping chamber.

SUMMARY OF THE INVENTION

The solution of this problem is effected in that a control device is provided which before each stroke change of the pump which opens the valve and after pressure equalization to ambient pressure, closes said valve and thereafter initiates the next stroke of the pump.

Compared with the known pump arrangement the pump arrangement according to the invention has the advantage that for given volumes of the pump housing and pump (i.e. the interior volume of the pump housing and the bellows volume) the predetermined pressure limits are necessarily reached, i.e. the pump operates completely satisfactorily.

This is because the respective starting pressure is the atmospheric pressure i.e. 1000 mbar.

Accordingly, with the above dimensions ($V_1 = 50$, $V_2 = 30$, $p_{min} = -400$ mbar and $p_{max} = 600$ mbar) the following pumping result is achieved:

(a) Pump at lower dead-center $V_1 = 0$ cm$^3$ $V_2 = 30$ cm$^3$ p=p abs.=1000 mbar.

This results on expansion in the following expansion pressure:

$p_E \times 1000 = 50 \times p_E$ $p_E = 600$ mbar abs. $= -400$ mbar rel.

(b) Pump at top dead-center $V_1 = 50$ cm$^3$ $V_2 = 0$ $p = 1000$ mbar

In the compression the following compression pressure $p_K$ is obtained:

$1000 \times 50 = p_K \times 30$ $p_K = 1665$ mbar abs., i.e. 665 mbar rel.

With the pump arrangement according to the invention a favorable ratio of pumping and bellows volume is thus reached. In addition, the pressures obtainable are defined by the ratio of the volumes and thus limited.

As a result the entire pump arrangement can be made substantially smaller and is nevertheless completely satisfactory during operation.

The pump arrangement according to the invention may advantageously be controlled as regards excess pressure and/or vacuum, for which purpose the known valves are used. In addition, by observing the entire pressure behaviour, which is advantageously stored in a memory, the entire system can be monitored and switched off when required.

BRIEF DESCRIPTION OF THE DRAWINGS

Further details, advantages and features will be explained in the following description with the aid of the drawings, wherein.

DESCRIPTION OF SPECIFIC EMBODIMENTS

Figure 1:
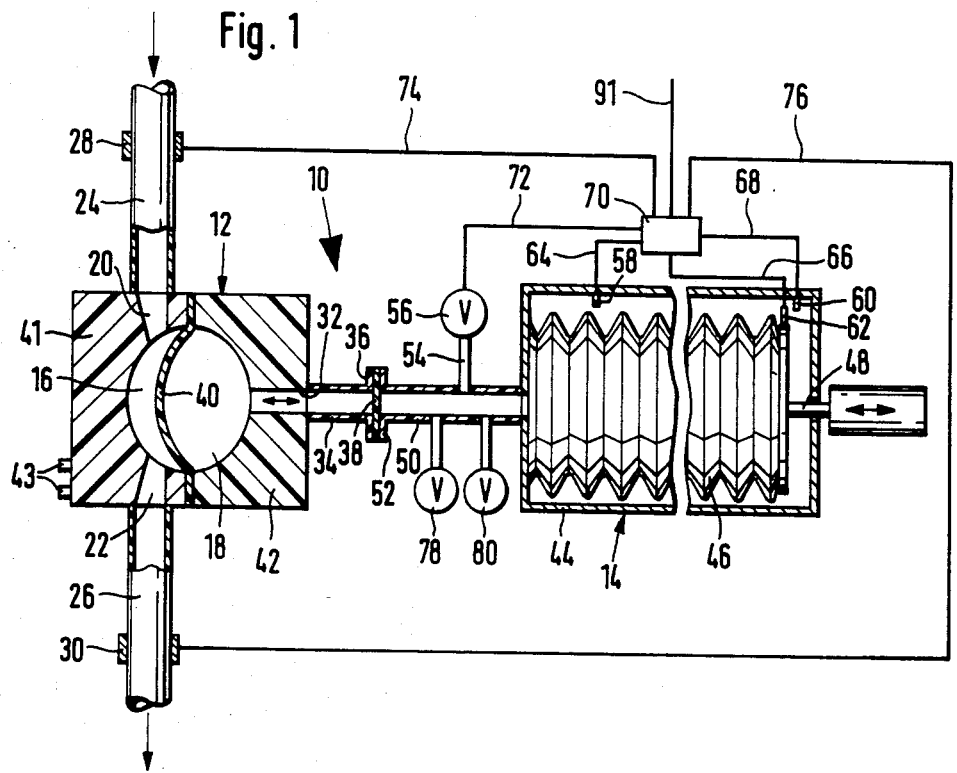
FIG. 1 shows a pump arrangement in cross section

In FIG. 1 the pump arrangement according to the invention is designated by 10. Said pump arrangement 10 comprises essentially a pump housing 12 and a pump 14 having a limited pumping volume, in particular a reciprocating piston pump or a bellows pump. The latter is illustrated in FIG. 1.

The pump housing comprises two chambers, a working chamber 16 for the liquid to be pumped and a drive chamber 18 for the fluid to be pumped in and out by the pump 16, in particular air.

The working chamber 16 comprises at least one first opening; in FIG. 1 two openings 20 and 22 are illustrated through which the liquid to be pumped is pumped into the first pumping chamber and out of the latter. The two openings 20 and 22 are connected respectively to flexible tubes 24 and 26 which are further connected to reservoirs and following means not shown on which the liquid to be pumped acts.

These flexible tubes 24 and 26 are provided with shut-off means 28 and 30, preferably electromagnetic tube clamps which are actuated in counter phase. Assuming that the tube 24 is to serve as liquid supply conduit and the tube 26 as liquid discharge conduit, the shut-off means 28 will be open in the filling phase whilst the shut-off means 30 is closed. In the emptying phase the converse is true, i.e. the clamp 30 is open and the clamp 28 closed.

The drive chamber 18 is also open towards the outside with a second opening 32 which like the other openings 20 and 22 passes through the pump housing so that through said opening 32 a pumping fluid can be pumped in and out.

This opening 32 is followed by a substantially rigid conduit 34 which preferably comprises at its end a flange 36. Said flange 36 advantageously secures a hydrophobic membrane 38 whose pores are so dimensioned that no germs can enter the conduit 34 and thus the drive chamber 18. This ensures that on breakage of the pump diaphragm 40 explained below the aqueous solution usually to be kept sterile does not flow through the conduit 34, which would make it unsterile. The membrane 38 serves as safety means in the case of breakage of the pump diaphragm 40. Such an arrangement is described in DE-OS No. 3,205,449.

Said pump diaphragm 40 divides the two pump chambers 16 and 18 and advantageously can have an already preformed curved shape. In this embodiment it can bear without extension on the respective walls of the chambers. In a further embodiment the pump diaphragm 40 has a planar form and can advantageously be disposed already biased a certain amount in the pump housing 12. In this case the diaphragm expands resiliently during pumping operation and tends on being relieved for example on venting of the pump 14 or opening of the clamps 28 and 30 to return to the initial state.

Advantageously, the pump housing 12 consists of two housing halves 41 and 42 between which in production the diaphragm is first inserted and which are then adhered or welded together. As material for the pump housing usually an easily moldable plastic material, for example PVC, polyacrylic glass or polycarbonate is chosen, whereas as material for the pump diaphragm soft PVC, polyethylene or the like, is used if the diaphragm is non-elastic, or elastic materials, such as silicone rubber, and the like.

The pump in volume $V_1$ is defined by the volumes of the two chambers 16 and 18. Advantageously, various standard volumes are used depending on the pumping rates which are to be generated.

Furthermore, it is preferred for the pumping housing 12 including the flexible tubes 24 and 26 and the conduit 34 connected thereto to be used as so called disposable component which is already in a sterile condition when it leaves the manufacturers.

In a first convenient embodiment the contour of the chambers 16 and 18 is identical as shown in FIG. 1.

Figure 2:
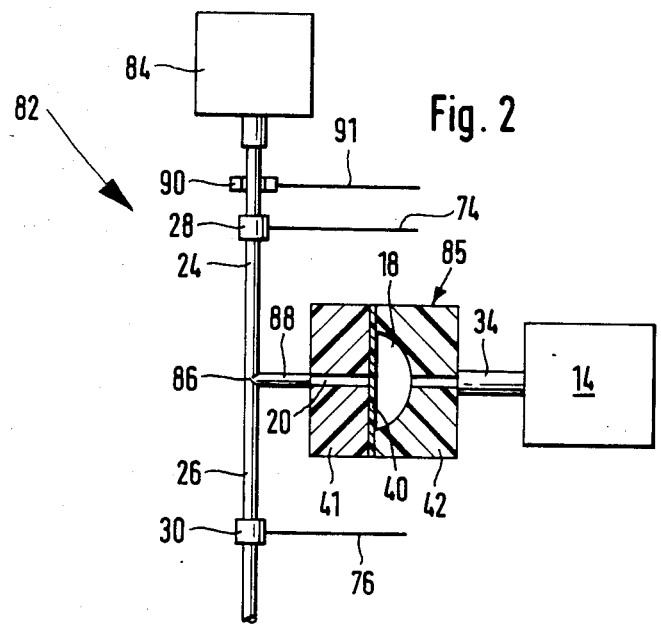
FIG. 2 shows diagrammatically an infusion apparatus with the pump arrangement.

On the other hand, however, in a further embodiment the contours of the chambers 16 and 18 may be asymmetrical. In FIG. 2 such an asymmetrical arrangement is shown in which advantageously as pumped diaphragm 40 a resilient or elastic pump diaphragm is used. In the embodiment shown in FIG. 2 the planar diaphragm bears directly on the chamber wall so that a second pump chamber is practically dispensed with and the second pump chamber as explained above is again connected to the pump 14. Provided the diaphragm chosen is sufficiently resilient such a pump can be referred to as self-exhausting.

Figure 3:
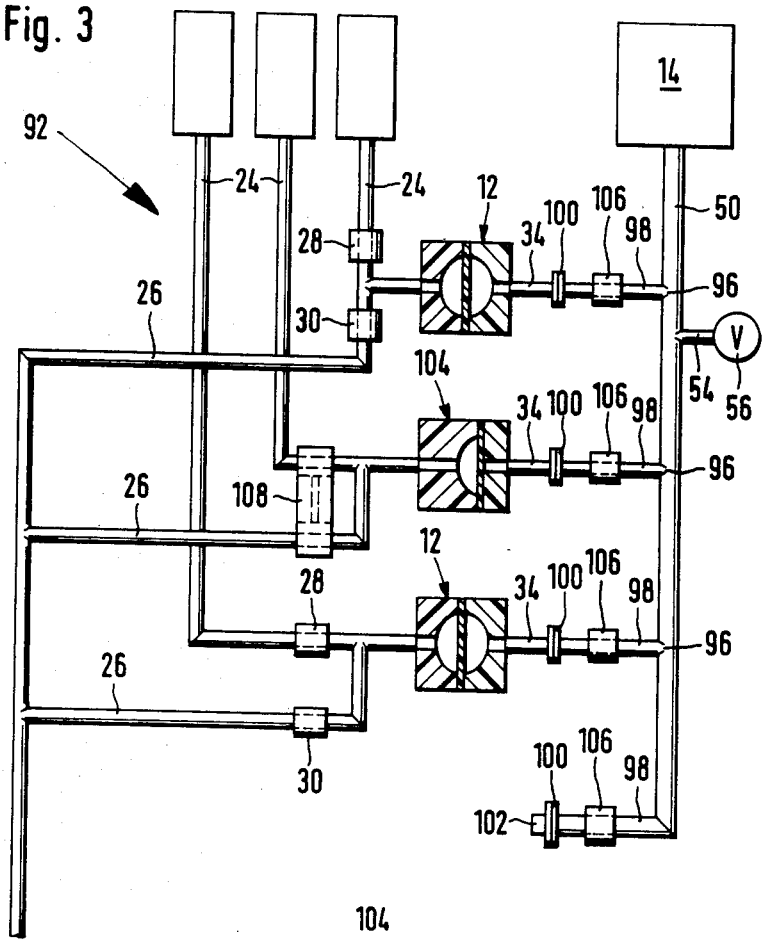
FIG. 3 shows diagrammatically another infusion arrangement with several pump housings and a bellows pump and FIG. 4 shows a specific embodiment of a pump housing.

On the other hand, however, the contour of the chambers 16 and 18 maybe such that the pump arrangement 10 is considered of self-suction type. Such a construction is shown in FIG. 3 in the middle pump arrangement. In this case the diaphragm lies on the side of the pump 14 on the planar wall so that the drive chamber 18 is not present in the non-loaded condition. In such an embodiment an elastic possibly prestressed pump diaphragm 40 is used.

As already explained above the pump arrangement 10 has a variable interior volume $V_1$. For fixing the pumping rate either the magnitude is entered into a control means in conjunction with the volume to be conveyed or alternatively the pump housing 12 comprises in dependence upon the volume $V_1$ specific code marks in the form of projections 43 at the outer wall which on insertion of the pump housing 12 into a control means which is not illustrated actuate a certain contact which leads to entering of the pumping volume $V_1$ in the control means. This is the case in particular with so called cassettes which are inserted into such a control device.

As shown in FIG. 1 the pump 14 is constructed as bellows pump and accordingly consists of a housing 44 in which a bellows 46 is inserted which by means of a reciprocating push rod 48 is compressed or expanded. The end of said bellows 46 is to be connected via a rigid conduit 50 whose end comprises a flange 52 to the pump housing 12, in particular to the conduit 34, the two flanges 36 and 52 being secured together.

Advantageously, the conduit 50 is closed in the uncoupled condition so that no air can escape therethrough. This is particularly of interest when the pump 14 is connected to several pump housings 12 via a conduit system as shown in FIG. 3. In such a case advantageously the conduit 50 is automatically closed whenever there is no connection to a pump housing 12 but opened when the connection is established, which can advantageously be achieved by an automatically acting valve arrangement as will be explained hereinafter.

A further conduit 54 which is closed with a valve 56 leads away from the conduit 50. Via said valve 56 the entire pump arrangement 10 can be vented so that the reduced or excess pressure obtaining in the pump arrangement 10 can be removed and the entire arrangement set to atmospheric pressure.

A particularly preferred embodiment of the invention resides in that the venting of the pump arrangement 10 takes place at the top and bottom dead-center of the pump 14.

For this purpose the housing 44 of the pump 14 is equipped with contacts 58 and 60 which cooperate with a contact 62 which is disposed on the bellows 46. These contacts are connected via lines 64, 66, 68 to the control device 70 which in turn is connected via a line 72 to the valve 56.

Furthermore, the control device is connected via a line 74 and a line 76 to the shut-off means 28 and 30 respectively.

Advantageously, at the bottom dead-center (compressed bellows 46) and at the top dead-center (expanded bellows) the control device 70 switches over the clamps 28 and 30, i.e. for filling the chamber 16 the clamp 28 is opened and the clamp 30 closed whilst for exhausting the chamber 16 the clamp 28 is closed and the clamp 30 is opened.

At the same time, advantageously, as already mentioned, in each case at these dead-centers the pump arrangement 10, in particular the drive chamber 18 and the interior of the bellows 46 is opened by opening the valve 56, which the control device 70 also initiates by closing the contacts 56–60, until pressure equalization in the pump arrangement 10. Advantageously, during this open phase the two clamps 28 and 30 are closed.

Advantageously, the pump arrangement is operated at certain limit pressures both in the reduced pressure range and in the excess pressure range. If these limit values are exceeded the pressure limiting valves 78 and 80 open and maintain a certain defined pressure limit value during the pumping phase of the pump 14. These pressure limiting valves 78 and 80 are automatically closed when the pump has reached its top or bottom dead-center. Such a pressure limiting arrangement is described in DE-OS No. 3,205,449 (corresponding to U.S. patent application Ser No. 466,645 filed Feb. 15, 1983) to the disclosure of which express reference is made.

This publication describes a further pump housing in which instead of a flat pump diaphragm 40 a hose-like pump diaphragm is used. Reference is again made to the disclosure of this pump diaphragm and the securing of said diaphragm in the pump housing.

As already explained at the beginning in this arrangement the reduced or excess pressure to be reached depends substantially on the ratio of the pumping volume $V_1$ and the volume $V_2$ of the expanded bellows 46. It is therefore easy to define the pressure limit value of the pressure limiting valves 78 and 80 which advantageously lies at least 10% above the respective pressure limit values defined on the basis of the arrangement chosen.

These pressure limit values are so chosen that the materials used can easily withstand these pressures. They lie in this respect in a range from 100 mbar–3 bar, preferably 400 mbar–2 bar.

On the other hand, these ranges may be exceeded if correspondingly strong materials are employed.

The pump arrangement 10 shown in FIG. 1 is operated in the following manner:

Via the tube 24 the fluid to be conveyed, for example blood or an infusion solution, is led from a container not illustrated to the pump housing 12. For this purpose the clamp 28 is open whilst the clamp 30 is closed. Furthermore, the bellows pump is at the bottom dead-center, i.e. at the left stop in accordance with the embodiment shown in FIG. 1. The pressure is also set to normal pressure. Thereafter the bellows is expanded, i.e. moved to the right, the expanded air also entraining the pump diaphragm 40 to the right. This produces a reduced pressure in the system which leads to fluid being pumped into the work chamber 16.. The pumping phase is completed when the chamber volume $V_1$ is completely filled with fluid, i.e. when the pump diaphragm 40 has engaged the right chamber wall. However, in this engagement the bellows 46 continues to move to the right until the top dead-center is reached. If the predetermined limit pressure value is exceeded the pressure limiting valve 78 opens automatically to keep a predetermined limit excess pressure value constant.

At the top dead-center the control device 70 first closes the clamp 28, opens the valve 56 for setting the pressure to normal pressure and then opens the clamp 30. At the same time the phase position of the pump 14 is switched over and the pump is changed to the compression phase, i.e. the pumping-off phase. Consequently, by the resulting excess pressure the pump diaphragm is moved to the left until it has come to bear on the wall of the left chamber half 16, i.e. until the condition of complete exhaustion is reached.

If a predetermined excess pressure is reached during the pumping phase itself the other pressure limiting valve 80 opens and keeps this excess pressure constant.

When the lower dead-center is reached the valve 56 is again actuated for setting to atmospheric pressure.

The filling phase then begins again.

In FIG. 2 a specific infusion apparatus is designated by 82, the same reference numerals as in FIG. 1 being used for corresponding parts.

This infusion apparatus 82 comprises an infusion bag 84 which is connected via the tube 24 to the pump housing 85 but which has only one opening 20 serving both as supply and discharge opening. Such an embodiment with only one opening is one of the preferred embodiments.

Accordingly, the tube 24 branches at the point 86 from which the tube 88 connected to the opening 20 and the tube 26 originate.

According to the pump arrangement shown in FIG. 2 the pump housing 85 comprises a drive chamber 18 which corresponds to the drive chamber 18 shown in FIG. 1. Likewise, the pump diaphragm 40 corresponds to the pump diaphragm 40 shown in FIG. 1. However, the working chamber 16 according to FIG. 1 is not present at all. Accordingly, the planar diaphragm 40 lies completely against the wall of the housing half 41.

Advantageously, in this embodiment a diaphragm is chosen which is resilient to such an extent that it is opened by the hydrostatic pressure in constrained manner provided the liquid column extends into the bag 84. However, the resilient return force should be dimensioned so that the pump diaphragm expands again only when the water column is at least 10 cm. Advantageously, the clamp 28 is disposed beneath this limit value, i.e. beneath about 10 cm, so that no air bubbles can form in the pump system, as is particularly important in infusion. The infusion apparatus 82 according to FIG. 2 is operated in the following manner:

With the clamp 28 opened the liquid disposed in the bag 84 urges the advantageously resilient pump diaphragm 40 to the right until said diaphragm 40 has come to bear on the wall of the right chamber half 42.

During this filling phase in accordance with a first embodiment the bellows pump 14 can support the filling operation, the valve 56 being actuated in the manner described in FIG. 1, i.e. opened only at the top and bottom dead-centers. However, according to a second embodiment the valve 56 can also be opened during the filling phase, i.e. the expansion of the bellows 46, this leading to automatic filling by the pressure of the water column. This embodiment is particularly preferred in the infusion apparatus 82 shown in FIG. 2.

When the filling is completed the bellows 46 is compressed with the valve 56 closed and vented at the bottom dead-center. The automatic filling phase then starts again.

It need not be particularly pointed out that instead of the asymmetric pump housing according to FIG. 2 the symmetric pump housing according to FIG. 1 may be used provided the diaphragm has the same elastic properties. However, in this case the return force of the diaphragm can lead to entraining of air bubbles into the working chamber 16 so that at the clamp 28 air sensors 90 are preferably disposed which are connected via the line 91 to the control device 70 and can switch off the entire apparatus.

In FIG. 3 a pump apparatus 92 is shown which has four connections for four pump housings, only three of which are occupied.

Once again, the conduit 50 leads away from the pump 14 and into said conduit 50 the valve 56 is connected via the conduit 54. According to the embodiment shown in FIG. 3 the conduit 50 comprises four branches 96 from which conduits 98 originate whose ends have connections 100. These connections 100 are advantageously equipped with a shut-off valve 102 which is opened on connection to the conduit 34.

As shown in FIG. 3 the pump apparatus 92 comprises two pump housings 12 of the type illustrated in FIG. 1 and an asymmetrical pump housing 104 which will be explained below.

Such pump apparatuses 92 are used particularly advantageously in intensive care where the patient has several infusion lines.

If in each case identical infusion rates are to be obtained pump housings 12, 104 having the same interior volume $V_1$ are preferably used, the pump being operated with a speed corresponding to the desired rate.

Depending on the bellows volume $V_2$ the pumping quantity $V_1$ increases advantageously either by the factors 2, 4, 8 etc. or by the factors 4, 16, 32 etc. The volumes $V_1$ and $V_2$ should be such that generally a continuous pumping rate can be obtained without appreciable pauses.

If however different pumping rates, i.e. different infusion solution amounts, are to be administered to the patient, in some cases pump housing 12, 104 with different volumes can be used, or pump housings 12 with the same volume provided the pauses are not too long and special precautions are taken to reduce the pumping rate. In this mode of operation of course the infusion rate with the highest pump frequency governs the speed and control. Thus if this pumping frequency leads to an excessive and thus undesirable pumping rate the following precautions can be taken:

If for example the infusion solution introduced into the other pump housing 12 according to FIG. 3 is to be infused in smaller amounts advantageously in the conduit connection 98 or 34 a shut-off means 106 is provided which shuts off these conduits accordingly. Thus, certain strokes of the bellows 46 and thus certain pumping steps can be omitted in that the shut-off means 106, preferably a valve or a tube clamp if flexible tubing is used, at the bottom dead-center of the pump 14 is closed for a predetermined period, for example until the pump 14 has reached the top dead-center.

Instead of the shut-off member 106 in another embodiment the clamp 30 can remain closed and when the clamp 28 is opened the pumping is back to the bag or when the clamp 28 is also closed only an increased vacuum is generated in the pump housing 12.

In a further embodiment it is also conceivable that on expansion of the bellows 46 the shut-off means 28 remains closed whilst the shut-off means 30 is opened. However, it must be ensured in such a case that no suckback from the other discharge conduits of the other pump housings occurs.

Possible shut-off means 28 and 30 or 106 are conventional magnetic or mechanical clamps, combined clamps being preferred for the two shut-off means 28 and 30. Such combination clamps in which always only one clamp is open whilst the other is necessarily closed are indicated by 108 is FIG. 3. This clamp 108 according to FIG. 3 is moved linearly between the two engagement points. However, it is also conceivable to provide a cam disposed on a disk which is moved in each case through a predetermined amount from the one closure position to the other closure position.

As explained above, these valves can be guided in constrained manner or controlled if electromagnetic valves are used.

Figure 4:
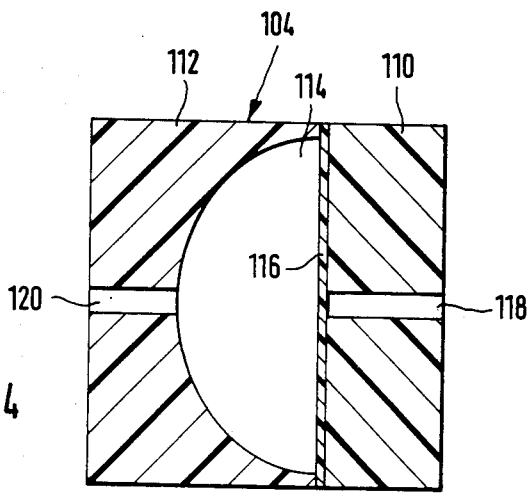

FIG. 4 shows to an enlarged scale the asymmetric pump housing 104 of FIG. 3. This pump housing 104 comprises a second chamber half 110 and a first chamber half 112, the chamber half 110 being in the form of a flat plate whilst the chamber half 112 comprises a hemispherical cavity 114. The two chamber halves are separated by the pump diaphragm 116. Additionally, the two chamber halves 110 and 112 comprise openings 118 and 120.

According to this embodiment the opening 118 is connected to the conduit 34 whilst the opening 120 is connected to the conduit 88.

As already explained above this pump form, provided a resiliently expandable diaphragm 116 is used, is self-resetting when the diaphragm 116 has come to bear fully on the inner wall of the pump housing 112 and the pump 14 is compressed.

In this mode of operation the valve 56 is preferably advantageously opened at the bottom dead-center and as a result the diaphragm 116 returns to the starting position. Consequently, the space 114 fills automatically with the pumping liquid. This is thus a self-suction pump.

If however, the opening 120 is connected to the pump 14 via the conduit 34 and the opening 118 is connected to the container for the liquid to be pumped via the conduit 88, the diaphragm 116 on expansion of the pump is entrained rearwardly until it has come to bear on the inner wall of the cavity 114. At the upper dead-center of the pump 14 (bellows pump or reciprocating piston pump) venting of the system then takes place by opening the valve 56 with the result that the diaphragm 116 returns to its starting position due to its resilient returning force and expels the stored liquid through the opening 118. This is thus a pump of the self-exhausting type.

The pump arrangements according to the invention may advantageously be connected to a microprocessor-controlled evaluation and/or control unit. The ratios of the amounts to be conveyed and the actual amounts may be programmed. Furthermore, these units may be programmable by the markings 43 themselves to the specific pump housing types, irrespective of whether symmetrical or asymmetrical pump housings are used.

I claim:

1. In an apparatus for pumping liquids for medical purposes, in particular blood fluid or infusion fluid, including at least one pump housing 12 having a cavity which is divided by an impermeable diaphragm into a working chamber (16) and a drive chamber (18), said working chamber being provided with at least one opening (2) for the supply and discharge of the fluid to be conveyed, and said drive chamber being adapted to be subjected to a gas as a pumping fluid and coupled via a conduit (50) of a limited pumping volume, the improvement comprising:
a valve means (56) connected to said drive chamber (18) for pressure compensation upon stroke change of the pumping means (46); and
a control means (70) connected to said valve means (56) and means responsive to the pumping means for controlling opening said valve means before each said stroke change and closing said valve means (56) after pressure equalization with ambient pressure.

2. The apparatus according to claim 1 wherein said response means includes position sensing means (58, 60, 62) coupled to said control means (70) for sensing position of said pumping means (46), where said valve means (56) is opened and closed by said control means (70) dependent upon signals conveyed by said position sensing means.

3. The apparatus according to claim 2, further including a first shut-off means (28) disposed upstream of the working chamber 6 (16) and a second shut-off means (30) disposed downstream of the working chamber (16) wherein the control means (70) is connected to the first shut-off means (28) and to the second shut-off means (30) and opens and closes said first shut-off means and said second shut-off means in a clocked manner.

4. The apparatus according to claim 3, wherein the first shut-off means (28) is closed or opened at the bottom or top dead-center of the pumping means (14) whereas the second shut-off means (30) is conversely opened or closed.

5. The apparatus according to claim 1, wherein the pumping means is equipped with reduced pressure and excess pressure limiting valves (78, 80).

6. The apparatus according to claim 1, further including a third shut-off means (106), wherein a connecting conduit between the drive chamber (18) of said at least one pump housing (12) and the pumping means (14) is opened or closed controlled by said third shut-off means (106).

7. The apparatus according to claim 6, wherein said at least one pump housing comprises a first and a second housing half.

8. The apparatus according to claim 7, characterized in that the first housing half comprises said at least one first opening for the supply and discharge of the liquid to be pumped and the second housing half comprises at least one second opening for the pumping fluid.

9. The apparatus according to claim 8, further including a a hydrophobic membrane (38) impermeable to germs and a substantially rigid conduit (34) wherein the second opening is connected to said substantially rigid conduit (34) the end of which is sealed with said hydrophobic membrane (38).

10. The apparatus according to claim 8, wherein said pump housing defines a pumping space and wherein the pumping space is asymmetrical.

11. The apparatus according to claim 10, the cavity is self-exhausting and the first housing half having the first opening (20) for the liquid to be pumped is constructed in the form of a plate on which the impermeable diaphragm bears in the unloaded state.

12. The apparatus according to claim 11, wherein the impermeable diaphragm is resilient to such an extent that the impermeable diaphragm expands only at a hydrostatic pressure of at least 10 cm WC.

13. The apparatus according to claim 10, wherein the cavity is of the self-suction type and the second housing half comprising having the second opening is constructed in the form of a plate upon which the impermeable diaphragm bears in area manner in the unloaded state.

14. The apparatus according to claim 10, wherein the pumping means operates during a filling phase and an exhaustion phase and wherein the valve (56) is to be opened during the filling phase.

15. The apparatus according to claim 10, wherein the pumping means operates during a filling phase and an exhaustion phase and wherein the valve (56) is to be opened during the exhaustion phase.

16. The apparatus according to claim 12, wherein the pumping means defines a first volume $V_1$ of said pumping space and a second volume $V_2$ of said pumping space and wherein the pump quantity $V_1$ defined by the volume of the working chamber (16) and by drive chamber (18) increases by a fixed ration relative to the volume $V_2$.

17. The apparatus according to claim 1, wherein the pump housing is a plastic disposable component and has code markings specifying the volume.

18. The apparatus according to claim 1, further including means for connecting and disconnecting the pumping means (14) via said conduit (50) to the at least one pump housing, said conduit (50) having a shut-off valve means (102) for closing the conduit (50) when said pumping means is disconnected from the at least one pump housing.

19. The apparatus according to claim 1, wherein a plurality of said at least one pump housing is connected to pumping means (14).

* * * * *